United States Patent [19]

Danzig et al.

[11] Patent Number: 4,806,149
[45] Date of Patent: Feb. 21, 1989

[54] METHOD FOR REGULATING PLANT GROWTH USING XANTHATES

[75] Inventors: Morris J. Danzig, Northbrook; Alan M. Kinnersley, Bedford Park, both of Ill.

[73] Assignee: CPC International Inc., Englewood Cliffs, N.J.

[21] Appl. No.: 105,936

[22] Filed: Oct. 8, 1987

[51] Int. Cl.$^4$ .................... A01N 37/00; C07C 154/02
[52] U.S. Cl. ...................................... 71/100; 558/244; 558/246
[58] Field of Search .................. 558/244, 246; 71/100

[56] References Cited

U.S. PATENT DOCUMENTS

| | | | |
|---|---|---|---|
| 3,148,049 | 9/1964 | Herschler | 71/100 |
| 3,994,950 | 11/1976 | Burke et al. | 558/246 |
| 4,427,436 | 1/1984 | D'Amico | 71/100 |

FOREIGN PATENT DOCUMENTS 1916054 10/1970 Fed. Rep. of Germany ........ 71/100

OTHER PUBLICATIONS

Morrison, et al., Organic Chemistry 3rd Ed., Allyn and Bacon, Inc., Boston, p. 1128, 1959.
Hawley, The Condensed Chemical Dictionary, 9th Ed, Van Nostrand Reinhold Co., N.Y., p. 930, 1976.
Fieser, et al., Advanced Organic Chemisty, Reinhold Publishing Corporation, N.Y., p. 142, 1977.
Mikami, et al, *Agr. Biol. Chem.*, 34, pp. 977-979 (1970).

*Primary Examiner*—John M. Ford
*Assistant Examiner*—Robert C. Whittenbaugh

[57] ABSTRACT

This invention relates to monoxanthates and dixanthates of dipropylene glycol and triethylene glycol. These xanthates increase both the rate of plant growth and the concentration of chlorophyll in the plants.

8 Claims, No Drawings

METHOD FOR REGULATING PLANT GROWTH USING XANTHATES

FIELD OF THE INVENTION

The present invention relates to new xanthates useful in a process for increasing the rate of plant growth and the chlorophyll concentration in plants. In this process, plants are treated with dilute solutions of the xanthates.

BACKGROUND OF THE INVENTION

Various derivatives of organic acids have been proposed as plant growth regulators. For example, West German Patent No. 19 16 054 discloses the use of alpha-hydroxy- or alpha-ketoalkanoic acids, having 7 to 10 carbon atoms, and their derivatives, particularly amides, for promoting the growth of plants under drought conditions. U.S. Pat. No. 3,148,049 discloses certain halogenated keto acids, such as halogenated acetoacetic acid, as plant growth regulators. In 1970, Mikami, et al, *Agr. Biol. Chem.*, 34, 977–979, reported test results of a number of hydroxy acids as plant growth regulators. Several of these, particularly, certain aromatic hydroxy acids, were shown to be root growth promoters. However, some of the simple acids, such as glycolic acid, caused suppression of root growth rather than root growth promotion. None of the hydroxy acids revealed any activity in the straight growth-promotion test used. U.S. Pat. No. 4,427,436 discloses the use of a heterocyclic xanthate, ethyl 3-benzothiazolinylmethyl xanthate, as an inhibitor for the growth of soybeans.

We have now discovered, to our surprise, that certain xanthates of glycols act as growth promoters and can increase chlorophyll concentration when applied to growing plants.

SUMMARY OF THE INVENTION

In accordance with this invention, there is provided a xanthate selected from the group consisting of dipropylene glycol xanthate, dipropylene glycol dixanthate, triethylene glycol xanthate, and triethylene glycol dixanthate.

Further provided in accordance with this invention, is a process for increasing the rate of growth of a plant which comprises supplying to the plant an effective amount of one or more xanthates selected from the group consisting of dipropylene glycol xanthate, dipropylene glycol dixanthate, triethylene glycol xanthate, and triethylene glycol dixanthate.

Also provided, in accordance with this invention, is a process for increasing the concentration of chlorophyll in a plant which comprises supplying to the plant an effective amount of one or more xanthates selected from the group consisting of dipropylene glycol xanthate, dipropylene glycol dixanthate, triethylene glycol xanthate, and triethylene glycol dixanthate.

DETAILED DESCRIPTION OF THE INVENTION

The activity of the xanthates used in the practice of this invention was discovered when they were tested in the duckweed promotion assay of Mitchell and Livingston, *Methods of Studying Plant Hormones and Growth-Regulating Substances*, USDA-ARS Agriculture Handbook, 336, pp. 66–67 (1968). This test showed that various xanthates have growth-promoting abilities when used in the concentration of between about 1 and about 500 ppm (parts per million) on a weight/volume basis. When the xanthates were present at concentrations of 0.1 ppm, no growth enhancement was observed. On the other hand, when xanthates were present at a concentration as high as 1000 ppm, growth inhibition was observed. For the xanthates tested, the optimum growth-promoting concentration was about 100 ppm.

An additional benefit derived from growing plants in the presence of the xanthates of this invention is that the plants accumulate more chlorophyll. The presence of such xanthates in the growth medium, particularly at concentrations of about 100 ppm on a weight/volume basis, greatly enhances the amount of chlorophyll accumulated per milligram of plant weight.

The xanthates generally useful in the practice of this invention are the mono- and dixanthates of dipropylene glycol and triethylene glycol. Mixtures of the xanthates may also be used.

Dipropylene glycol xanthate is represented by the formula

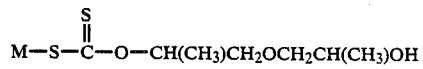

where M is sodium or potassium. Dipropylene glycol dixanthate is represented by the formula

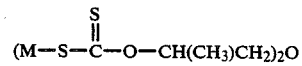

where M is sodium or potassium. Triethylene glycol xanthate is represented by the formula

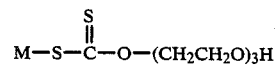

where M is sodium or potassium. Triethylene glycol dixanthate is represented by the formula

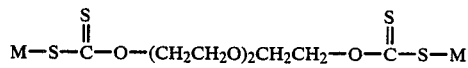

where M is sodium or potassium.

As noted above, the activity of the xanthates used in the practice of this invention was discovered when they were tested in the duckweed promotion assay. Since this assay involves growing the plants on an aqueous solution, it demonstrates the usefulness of the process in promoting the growth of plants in hydroponic culture. Likewise, the process of this invention is useful when plants are propagated by means of tissue culture. This is a particularly useful application of these xanthates, since many plants are now propagated commercially by means of tissue culture.

The xanthates used in the process of the present invention are seen to produce more than one growth-regulating effect on the plants. The particular growth-regulating effect produced by a plant depends, of course, on a number of variables, including the xanthate or mixture of xanthates used, the concentration and total amounts of the xanthates used, the time at which the xanthates are applied, and the type of plant species which is treated. The amount of material added is the effective amount needed to obtain the response desired. In general, the xanthates are utilized in dilute aqueous solutions which contain the xanthates in concentrations of from about 1 to about 500 ppm on a weight/volume basis. For most applications, the preferred concentrations are from about 10 ppm to about 100 ppm. The most suitable concentrations for a particular application are readily determined by well-known screening tests, such as those given in the examples.

Solutions of the xanthates are conveniently applied to the plants in the water added for plant growth. This water may also contain nutrients required by the plants. Optionally, solutions of the xanthates may be sprayed onto or otherwise applied to the roots, stems, or leaves of the plants.

The following specific examples illustrate the present invention. They are not intended to limit the invention in any way. When concentrations are given in ppm, they are on a weight/volume basis. The dipropylene glycol used as a starting material and for comparative tests was obtained from the Aldrich Chemical Company, Milwaukee, Wis. The diethylene glycol used as a starting material was obtained from the Union Carbide Corporation, New York City. The monoxanthates were prepared by the slow addition of 1 mole of caron disulfide to a solution of 1 mole of the glycol dissolved in a 50% aqueous solution containing 1 mole of potassium hydroxide. The mixture was cooled in ice and stirred during the addition. After the addition, the mixture was allowed to warm to room temperature for 1 hour with stirring. The crude reaction mixtures were purified by dilution with 50 parts of isopropyl alcohol before the mixture was filtered and the mother liquor was concentrated by evaporation under reduced pressure at 55° C. Residual solvent was removed from the mixture by extraction with ether and ethyl acetate. The residual xanthate was a heavy syrup. Dixanthates of the glycols were prepared in a similar manner to that used for the monoxanthates except that 2 moles of potassium hydroxide and 2 moles of carbon disulfide were used per mole of glycol. The presence of the xanthate group in each of the compounds was shown by $C^{13}$ NMR analysis.

EXAMPLE 1

Duckweed (*Lemna minor L.*) was grown following the general procedure of Mitchell and Livingston, *Methods of Studying Plant Hormones and Growth Regulating Substances*, USDA-ARS Agriculture Handbook, 336, pp. 66-67 (1968). Plants were grown on Nickell's medium as described in the handbook with the iron being present as the ferrous ion chelated with EDTA. One plant at the three-frond stage was placed in each flask. Flasks were incubated at 25° C. for 16-18 days under 300- to 500-foot candles of light for 16 hours per day. The plants were harvested and dried before plant weight was measured. All reported values represent 3 to 5 replicates.

Experiments were performed in which various concentrations of the xanthates were added to the duckweed growth medium. A control was run in which no xanthate was added. The results given in Table I demonstrate that growth is greatly enhanced when comparatively small concentrations of the xanthates are present in the medium. Higher concentrations of the xanthates show a growth-inhibiting action.

The comparative test also shows that a starting glycol from which xanthates were prepared shows no growth-promoting activity at the concentrations tested.

TABLE I

DUCKWEED GROWTH ASSAY

| | Dry Weight (mg) | | | | | |
|---|---|---|---|---|---|---|
| Additive (ppm) | 0 (Control) | 0.1 | 1 | 10 | 100 | 1000 |
| Dipropylene[a] Glycol | 29 ± 5 | | | 23 ± 13 | 20 ± 2 | 20 ± 3 |
| Dipropylene Glycol Xanthate | 43 ± 6 26 ± 6 | 41 ± 5 | 50 ± 4 | 56 ± 1 37 ± 4 | 40 ± 2 | 20 ± 5 |
| Dipropylene Glycol Dixanthate | 43 ± 6 26 ± 6 | 36 ± 7 | 48 ± 4 | 52 ± 6 33 ± 1 | 39 ± 5 | 11 ± 3 |
| Triethylene Glycol Xanthate | 43 ± 6 | 43 ± 4 | 45 ± 4 | 54 ± 5 | | |
| Triethylene Glycol Dixanthate | 43 ± 6 36 ± 7 | 43 ± 6 | 47 ± 5 52 ± 6 | 54 ± 13 71 ± 8 | 88 ± 11 | 44 ± 5[b] |

[a]Comparative test - not an example of this invention.
[b]Dixanthate concentration was 500 ppm.

EXAMPLE 2

The general procedure of Example 1 was followed and the chlorophyll content of the harvested plants was determined by the method of Kirk, Planta, 78, 200-207 (1968) Samples of the preweighed dried duckweed were suspended in 80% acetone. The mixture was homogenized for 30 seconds using a POLYTRON® Brand Homogenizer (Brinkman Instruments, Westbury, N.Y.). The mixture was centrifuged and absorption of the supernatant was read at 663 and 645 nm. From these readings, the number of micrograms of chlorophyll per milligram of dry weight was determined using the nomogram of Kirk. The results given in Table II show that the xanthates used in the process of this invention increase the chlorophyll content of plants. The increase in chlorophyll content is especially noted when the xanthates are present in the growth medium in concentration of about 100 ppm.

TABLE II

DUCKWEED CHLOROPHYLL CONCENTRATION ASSAY

| | Chlorophyll (µg/mg) | | | |
|---|---|---|---|---|
| Xanthate | 0 (Control) | 10 ppm | 100 ppm | 1000 ppm |
| Dipropylene Glycol Xanthate | 2.8 2.0 | 4.1 2.2[a] | 5.9 4.4[a] | 4.9 5.1[a] |
| Dipropylene Glycol Dixanthate | 2.8 2.0 | 3.4 3.4[a] | 6.6 5.2[a] | 3.4 3.2[a] |
| Triethylene | 2.0 | 2.8[a] | 5.5[a] | 3.9[a] |

TABLE II-continued

DUCKWEED CHLOROPHYLL CONCENTRATION ASSAY

| Xanthate | Chlorophyll ($\mu$g/mg) | | | |
| --- | --- | --- | --- | --- |
|  | 0 (Control) | 10 ppm | 100 ppm | 1000 ppm |
| Glycol Xanthate Triethylene Glycol Dixanthate | 2.0 | 2.3[a] | 5.4[a] | 2.7[a] |

[a]This test employed crude (unpurified) xanthate.

Thus, it is apparent that there has been provided, in accordance with the invention, an improved process for increasing the rate of plant growth and for increasing the chlorophyll content of plants which fully satisfies the objects, aims, and advantages set forth above. While the invention has been described in conjunction with specific embodiments thereof, it is evident that many alternatives, modifications, and variations will be apparent to those skilled in the art in light of the foregoing description. Accordingly, it is intended to include all such alternatives, modifications, and variations as set forth within the spirit and scope of the appended claims.

What is claimed is:

1. A xanthate selected from the group consisting of dipropylene glycol xanthate, dipropylene glycol dixanthate, triethylene glycol xanthate, and triethylene glycol dixanthate.

2. A process for increasing the rate of growth of a plant which comprises supplying to the plant an effective amount of one or more xanthates selected from the group consisting of dipropylene glycol xanthate, dipropylene glycol dixanthate, triethylene glycol xanthate, and triethylene glycol dixanthate.

3. The process of claim 2 wherein the xanthate is supplied to the plant in an aqueous solution at a concentration of between about 1 and about 500 parts per million on a weight/volume basis.

4. The process of claim 3 wherein the plant is *Lemna minor* L.

5. The process of claim 2 wherein the plant is grown in hydroponic or tissue culture.

6. A process for increasing the concentration of chlorophyll in a plant which comprises supplying to the plant an effective amount of one or more xanthates selected from the group consisting of dipropylene glycol xanthate, dipropylene glycol dixanthate, triethylene glycol xanthate, and triethylene glycol dixanthate.

7. The process of claim 6 wherein the xanthate is supplied to the plant in an aqueous solution at a concentration of between about 1 and about 500 parts per million on a weight/volume basis.

8. The process of claim 7 wherein the plant is *Lemna minor* L.

* * * * *